United States Patent
Kishore et al.

(10) Patent No.: US 10,107,795 B2
(45) Date of Patent: *Oct. 23, 2018

(54) COMPOSITION AND METHODS FOR THE PREVENTION AND TREATMENT OF DIET-INDUCED OBESITY

(71) Applicant: UNITED STATES OF AMERICA AS REPRESENTED BY THE DEPARTMENT OF VETERANS AFFAIRS, Washington, DC (US)

(72) Inventors: Bellamkonda K. Kishore, Washington, DC (US); Yue Zhang, Washington, DC (US); Carolyn M. Ecelbarger, Washington, DC (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 8 days.

This patent is subject to a terminal disclaimer.

(21) Appl. No.: 14/438,854

(22) PCT Filed: Oct. 25, 2013

(86) PCT No.: PCT/US2013/066932
§ 371 (c)(1),
(2) Date: Apr. 27, 2015

(87) PCT Pub. No.: WO2014/066830
PCT Pub. Date: May 1, 2014

(65) Prior Publication Data
US 2015/0259692 A1   Sep. 17, 2015

Related U.S. Application Data

(60) Provisional application No. 61/795,815, filed on Oct. 25, 2012.

(51) Int. Cl.
| | | |
|---|---|---|
| *C12N 15/113* | (2010.01) | |
| *A61K 31/7088* | (2006.01) | |
| *A61K 31/01* | (2006.01) | |
| *G01N 33/50* | (2006.01) | |
| *A01K 67/027* | (2006.01) | |
| *C07K 16/28* | (2006.01) | |
| *A61K 38/46* | (2006.01) | |
| *A61K 47/26* | (2006.01) | |

(52) U.S. Cl.
CPC ..... *G01N 33/5044* (2013.01); *A01K 67/0276* (2013.01); *A61K 38/465* (2013.01); *A61K 47/26* (2013.01); *C07K 16/28* (2013.01); *C12N 15/1138* (2013.01); *C12Y 301/00* (2013.01); *A01K 2207/25* (2013.01); *A01K 2217/075* (2013.01); *A01K 2227/105* (2013.01); *A01K 2267/0362* (2013.01); *C07K 2317/76* (2013.01); *C12N 2310/11* (2013.01); *C12N 2310/12* (2013.01); *C12N 2310/14* (2013.01); *C12N 2310/531* (2013.01); *C12N 2320/30* (2013.01)

(58) Field of Classification Search
None
See application file for complete search history.

(56) References Cited

U.S. PATENT DOCUMENTS

| 6,372,724 B1 | 4/2002 | Pelleg et al. | |
|---|---|---|---|
| 9,072,766 B2 * | 7/2015 | Kahn | C12N 15/1137 |
| 2009/0297497 A1 | 12/2009 | Kishore et al. | |

FOREIGN PATENT DOCUMENTS

| WO | 2005100990 A2 | 10/2005 |
|---|---|---|
| WO | WO2006052007 * | 5/2006 |
| WO | 2014066830 A1 | 5/2014 |

OTHER PUBLICATIONS

Crooke et al (Molecular Vision 2009; 15:1169-1178).*
Partial manual translation of WO2006052007, May 2006.*
Geary (Expert Opin. Drug Metab. Toxicol. (2009) 5(4): 381-391) (Year: 2009).*
Lundquist (Islet lysosomal enzyme activities and plasma insulin levels in obese hyperglycemic mice following the injection of the lysosomotropic drug suramin, Diabetes Res. 2: 207-211, 1985) (Year: 1985).*
International Search Report and Written Opinion for related International Application No. PCT/US20131066932 dated Jan. 28, 2014, in 11 pages.

* cited by examiner

*Primary Examiner* — Richard A Schnizer
(74) *Attorney, Agent, or Firm* — Adriano & Associates

(57) ABSTRACT

Blunting the activity of the P2Y$_2$ receptor results in a resistance to diet-induced obesity, an increased metabolic rate, and a better glucose tolerance. Compounds that inhibit the puringeric P2Y$_2$ receptor are useful for treating disorders associated with diabetes, treating obesity, and increasing metabolism (e.g., fatty acid metabolism).

7 Claims, 13 Drawing Sheets

Fig. 1A: Change in Body Weight of Wild Type (WT) and P2Y$_2$ knockout (KO) Mice fed Regular Diet (CNT) or High-Fat Diet (HFD) for 16 Weeks with ad libitum Access to Food and Drinking Water
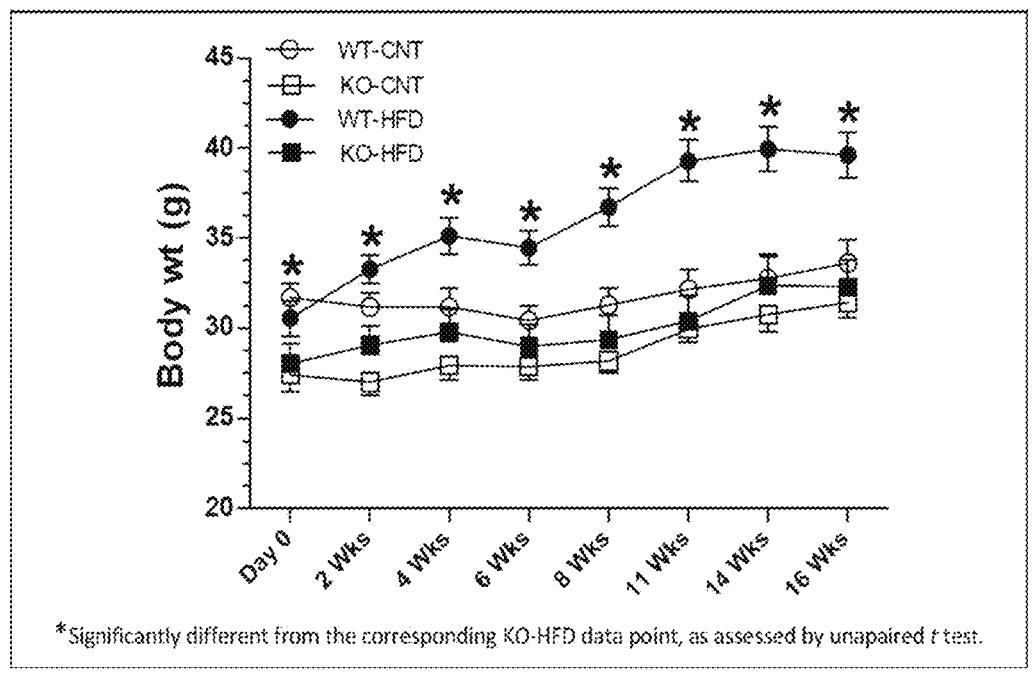
*Significantly different from the corresponding KO-HFD data point, as assessed by unpaired t test.
Fig. 1B: Body Weights of Wild Type (WT) and P2Y$_2$ Knockout (KO) Mice fed High-Fat Diet for 16 Weeks
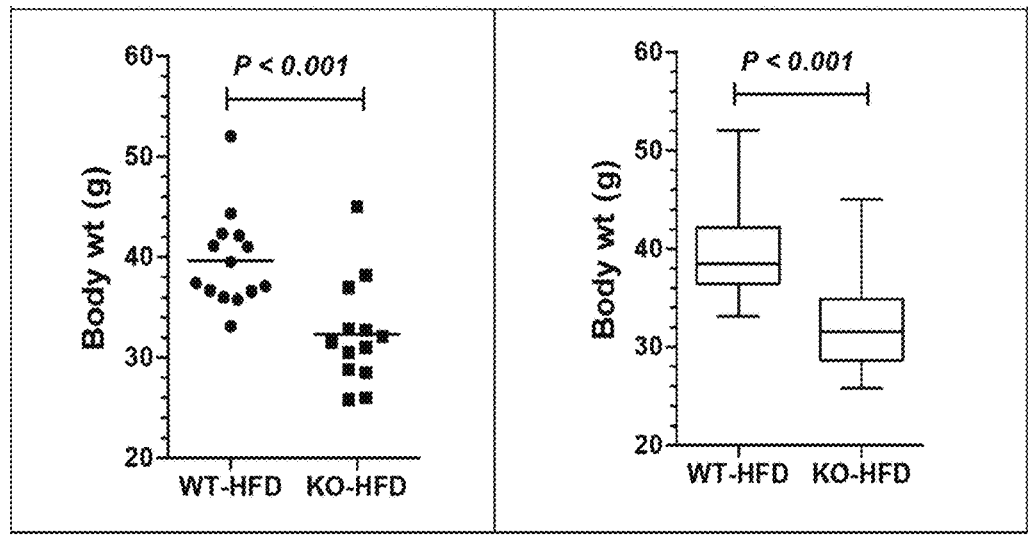

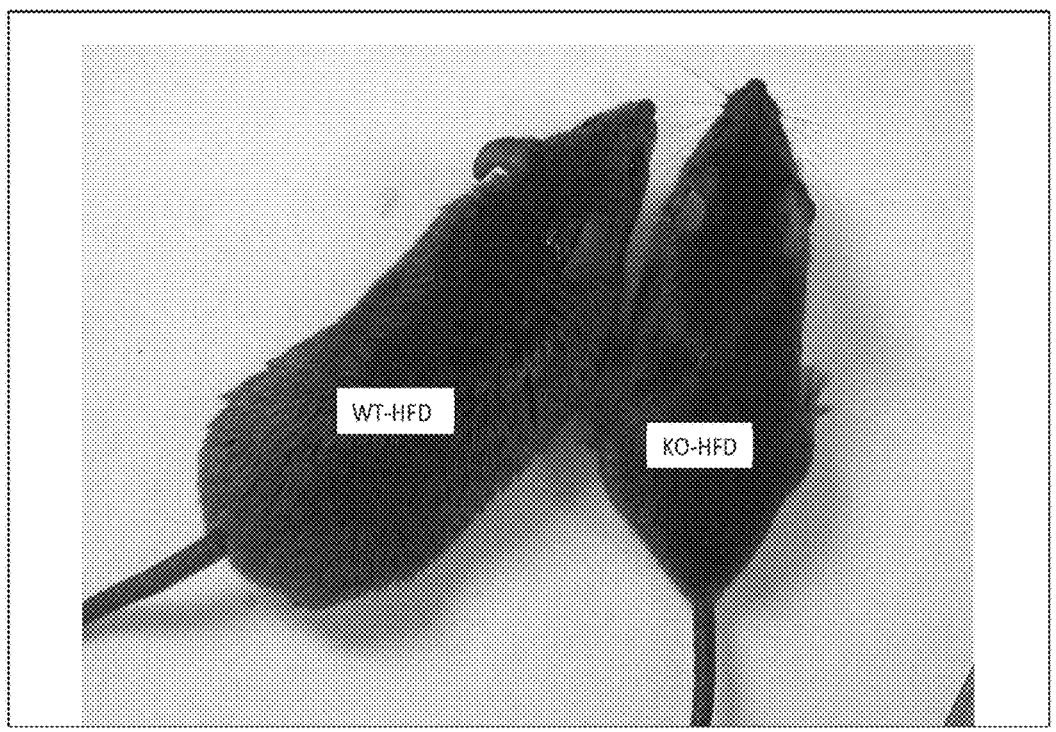
Fig. 2: Comparison of size of one of the highest weighing wild type mice from the high-fat diet group (WT-HFD) with an average weighing knockout mouse from the high-fat diet fed group (KO-HFD).

Fig. 3A: Food Intake of Wild Type (WT) and P2Y$_2$ knockout (KO) Mice on Regular Diet (CNT) or High-Fat Diet (HFD) Determined after 4 Weeks of Start of the Experimental Period (Expressed as g/day)
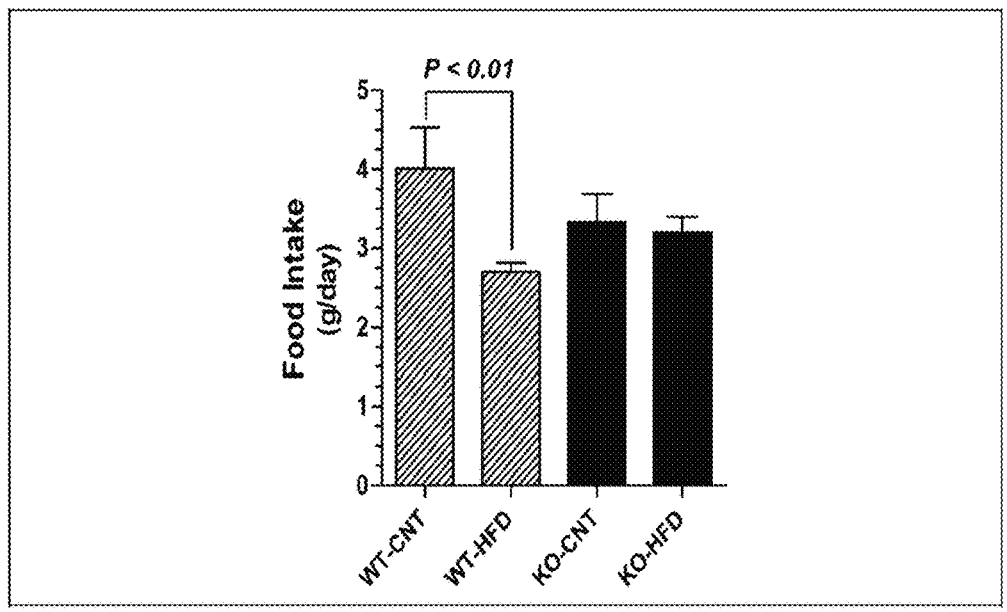
Fig. 3B: Food Intake of Wild Type (WT) and P2Y$_2$ knockout (KO) Mice fed High-Fat Diet (HFD) for 12 Weeks (Expressed as g/day or g/g body weight)
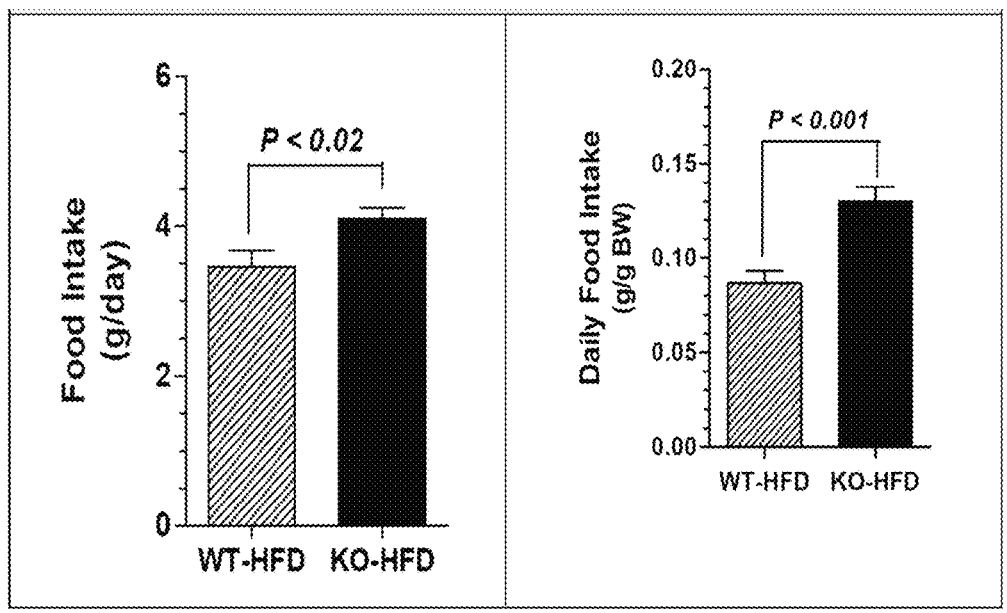

Fig. 4A: Water Intake by Wild Type (WT) and P2Y$_2$ knockout (KO) Mice fed Regular Diet (CNT) or High-Fat Diet (HFD) for 4 Weeks with ad libitum Access to Food and Drinking Water
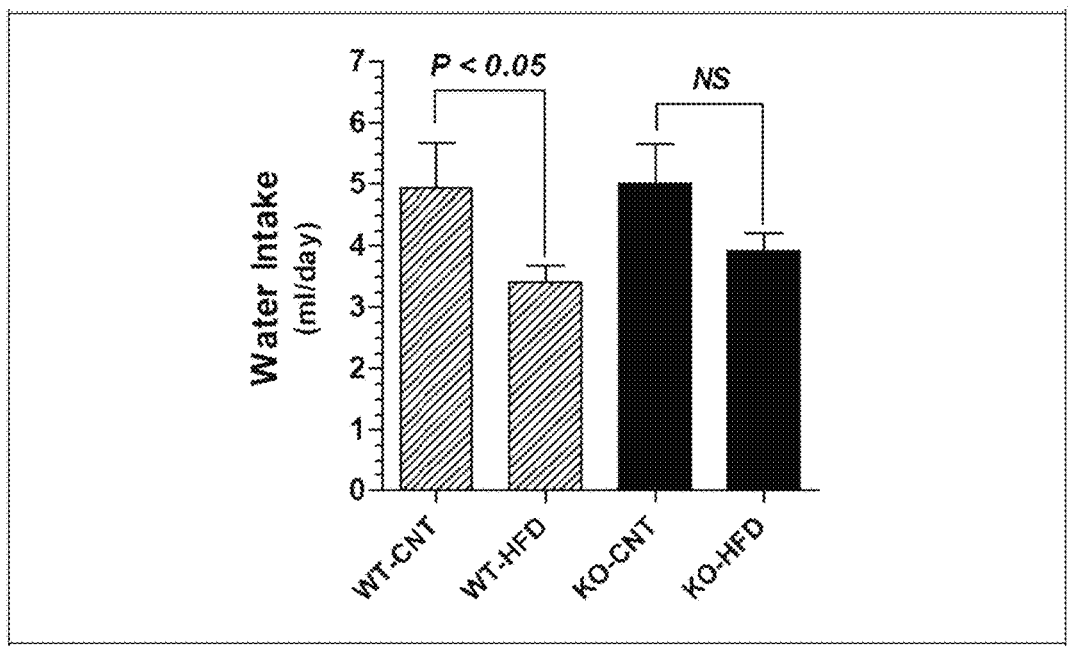
Fig. 4B: Water Intake by Wild Type (WT) and P2Y$_2$ knockout (KO) Mice fed High-Fat Diet for 12 Weeks
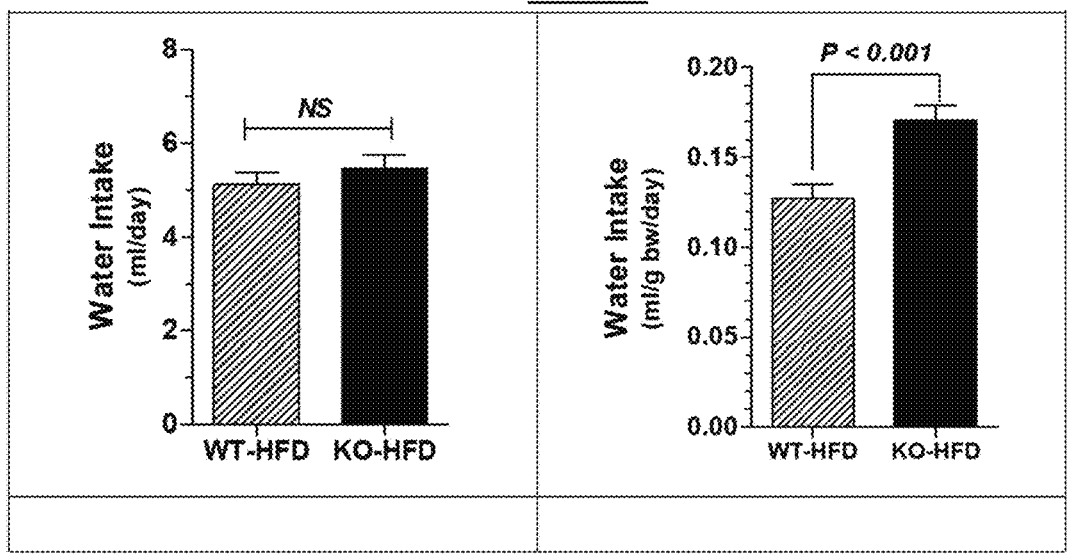

Fig. 5A: Urine Output and Urine Osmolality in Wild Type (WT) and P2Y$_2$ knockout (KO) Mice fed Regular Diet (CNT) or High-Fat Diet (HFD) for 4 Weeks with ad libitum Access to Food and Drinking Water
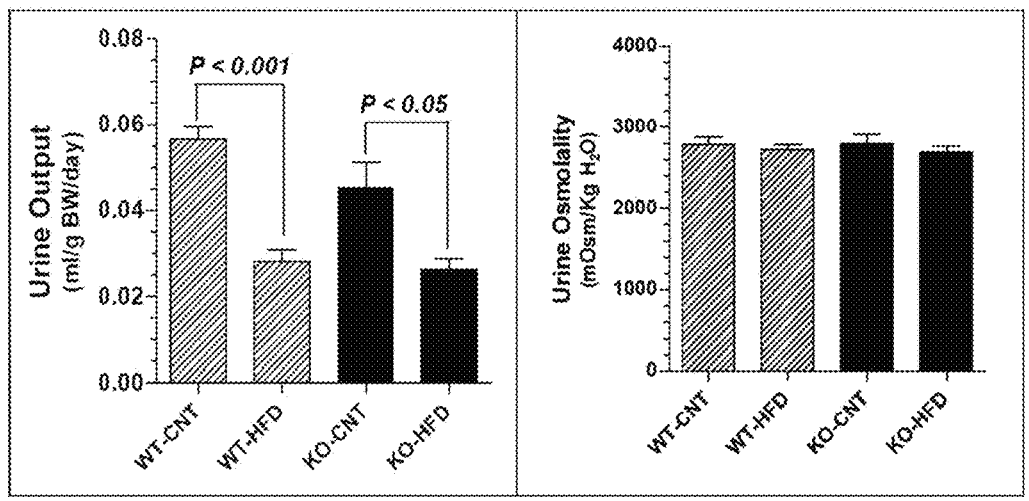
Fig. 5B: Urine Output and Urine Osmolality in Wild Type (WT) and P2Y$_2$ knockout (KO) Mice fed High-Fat Diet (HFD) for 12 Weeks with ad libitum Access to Food and Drinking Water
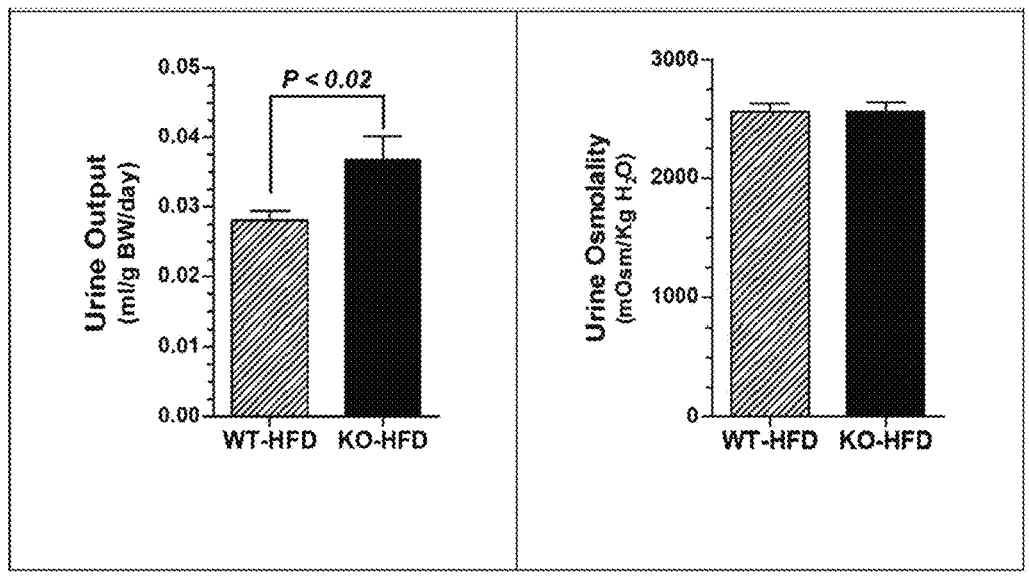

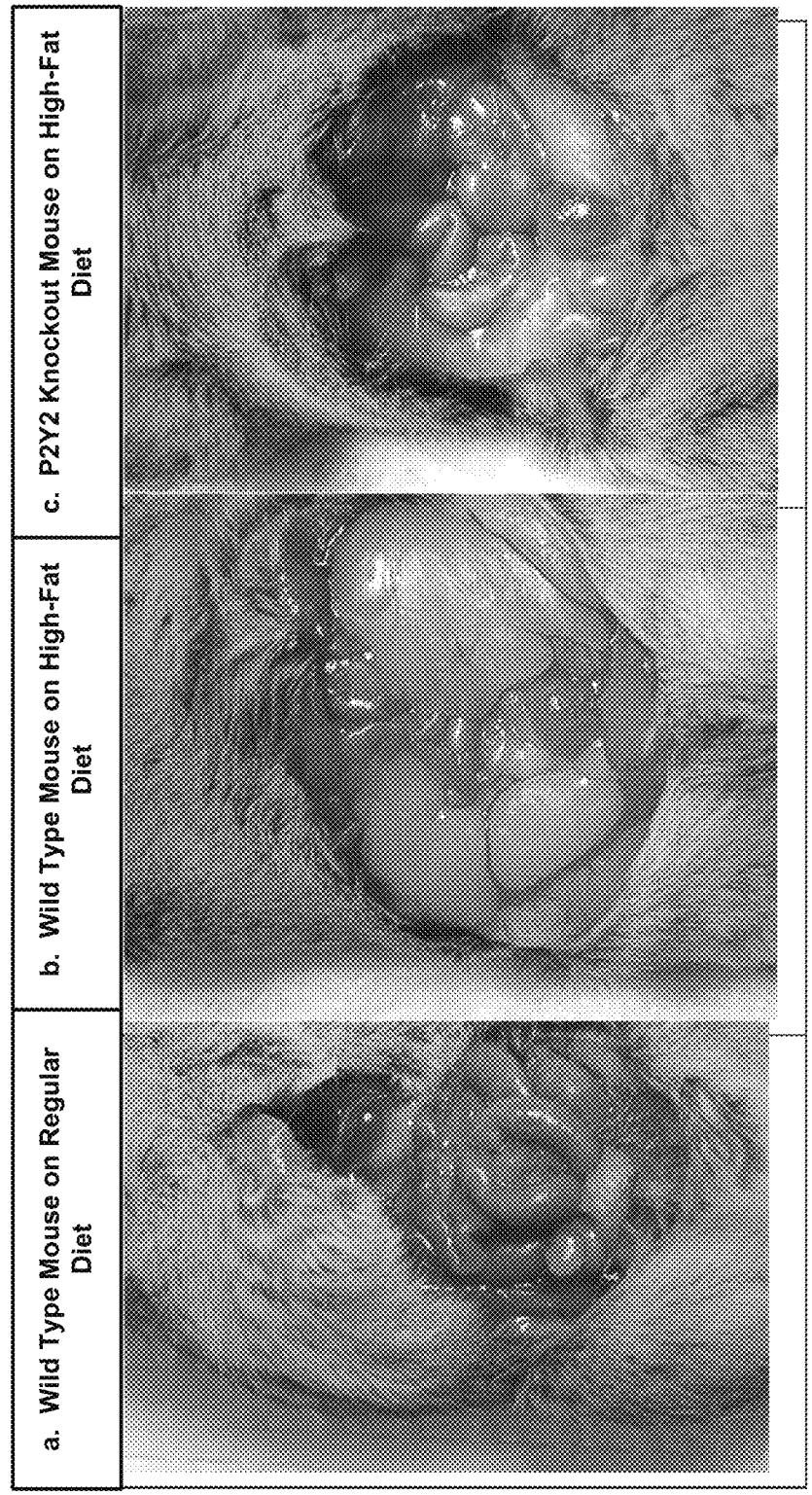
Fig. 6A: Appearance of Abdominal Fat at the Time of Euthanasia (Terminal)
a. Wild Type Mouse on Regular Diet
b. Wild Type Mouse on High-Fat Diet
c. P2Y2 Knockout Mouse on High-Fat Diet Fig. 6B: Representative pictures of white fat obtained from high-fat diet fed wild type mouse (left panel) and knockout mouse (right panel)
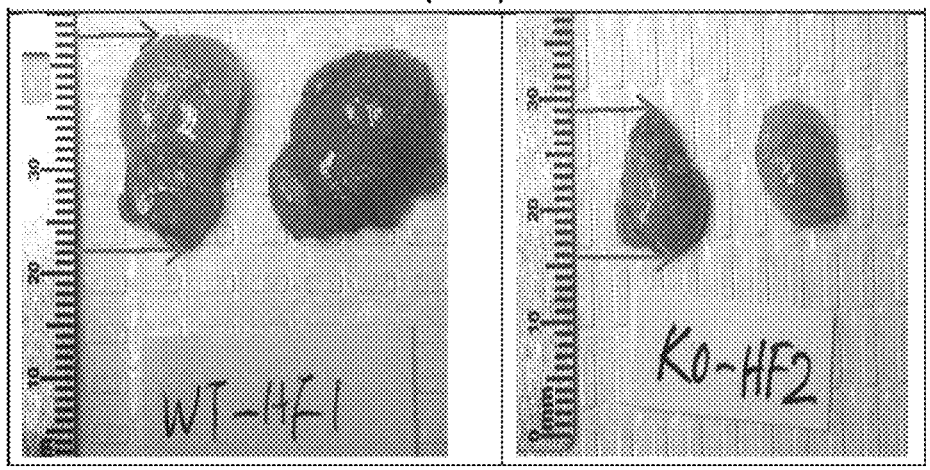
Fig. 6C: Representative pictures of brown fat obtained from high-fat diet fed wild type mouse (left panel) and knockout mouse (right panel)
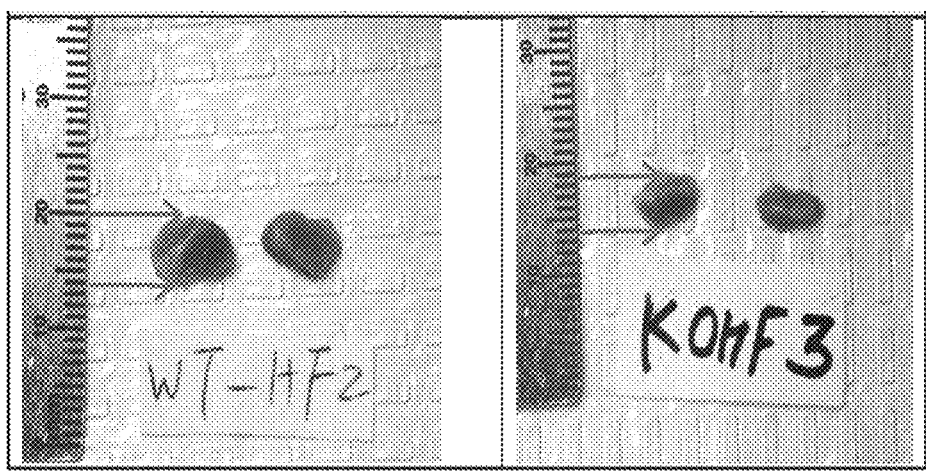

Fig. 7A: Terminal Weight of White Adipose Tissue in Wild Type (WT) and $P2Y_2$ knockout (KO) Mice fed Regular Diet (CNT) or High-Fat Diet (HFD) with ad libitum Access to Food and Drinking Water
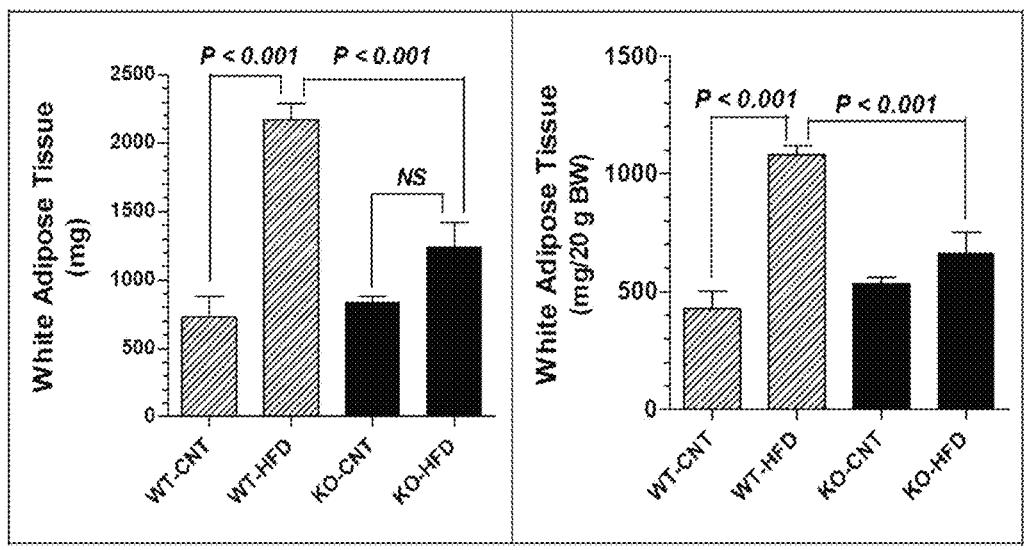
Fig. 7B: Terminal Weight of Brown Adipose Tissue in Wild Type (WT) and $P2Y_2$ knockout (KO) Mice fed High-Fat Diet (HFD) with ad libitum Access to Food and Drinking Water
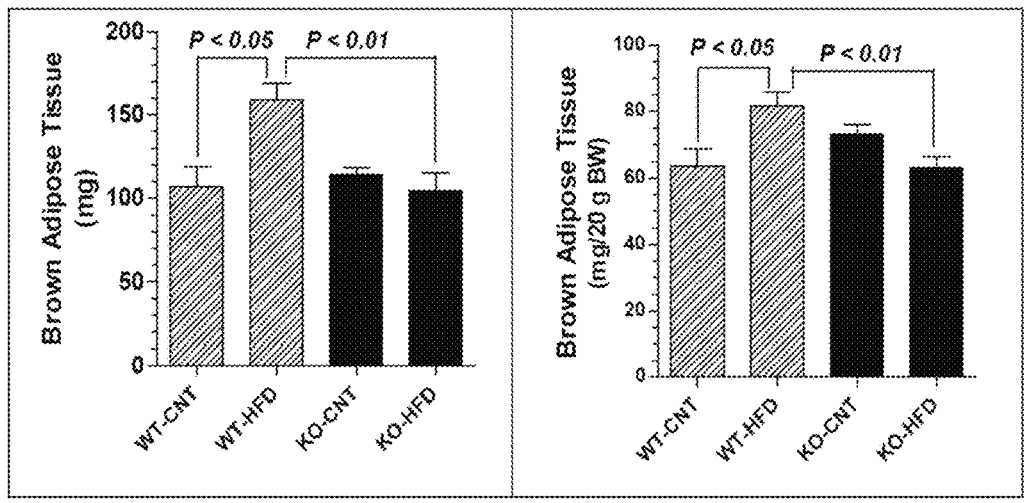

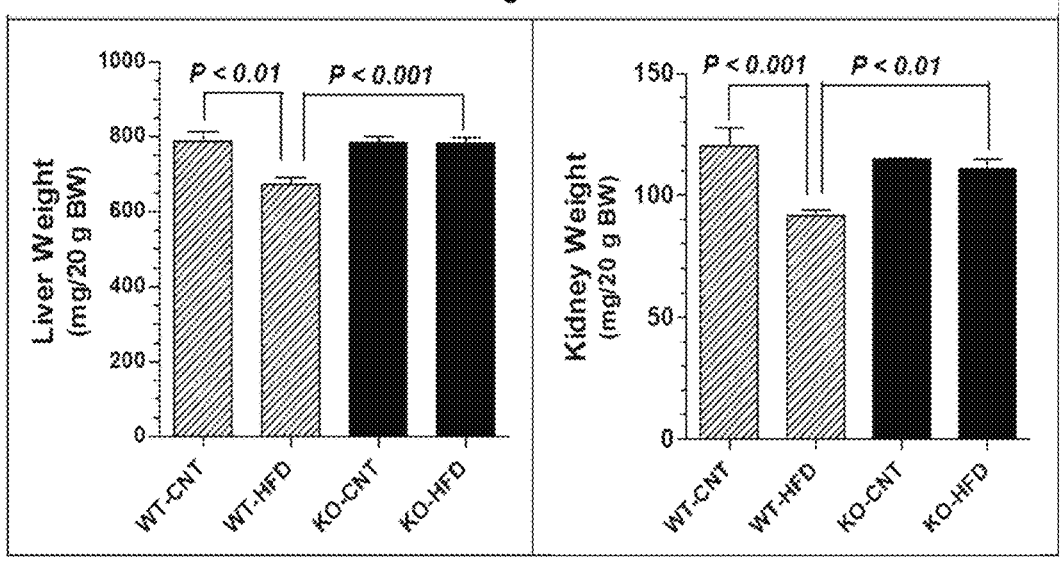
Fig. 8: Terminal Weight of Liver and Kidney in Wild Type (WT) and $P2Y_2$ knockout (KO) Mice fed Regular Diet (CNT) or High-Fat Diet (HFD) with ad libitum Access to Food and Drinking Water for 16 weeks.

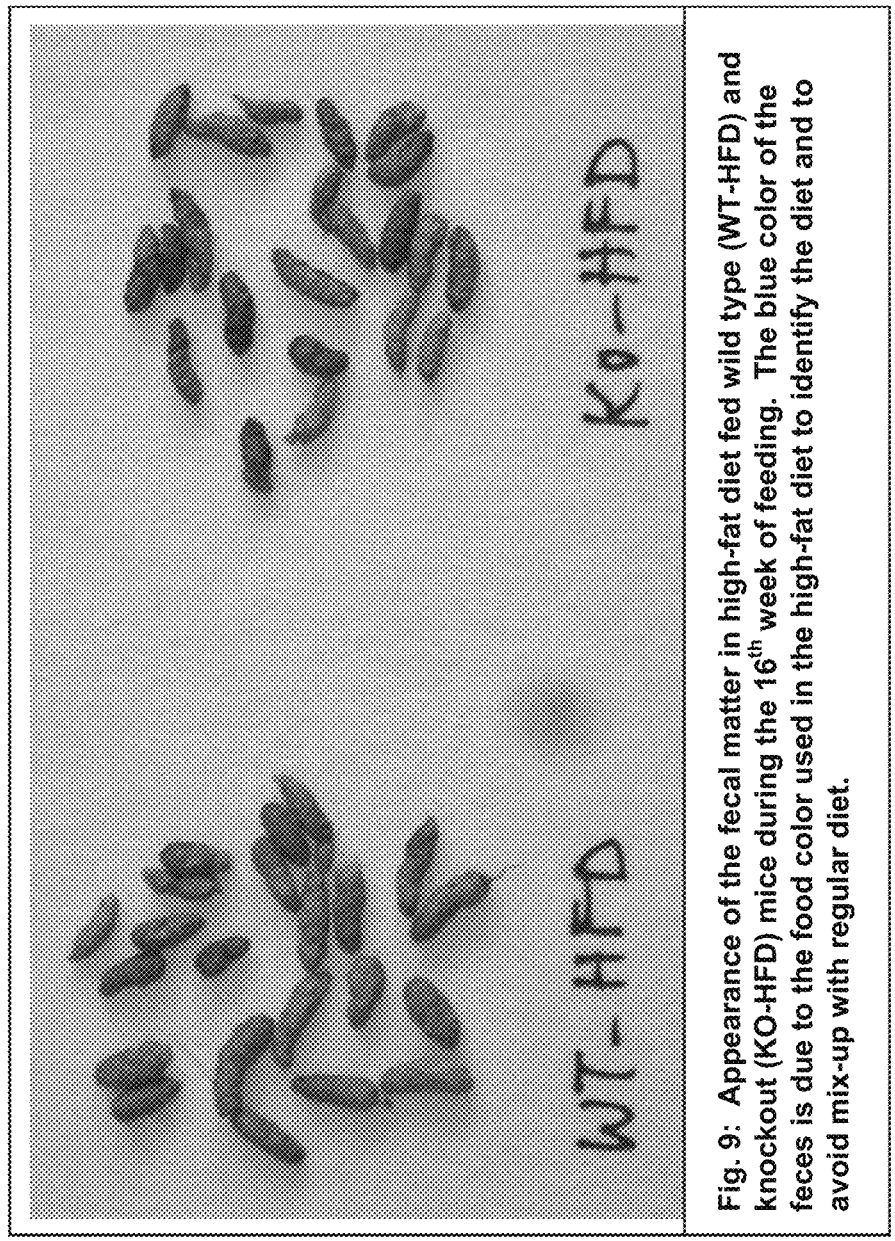
Fig. 9: Appearance of the fecal matter in high-fat diet fed wild type (WT-HFD) and knockout (KO-HFD) mice during the 16$^{th}$ week of feeding. The blue color of the feces is due to the food color used in the high-fat diet to identify the diet and to avoid mix-up with regular diet.

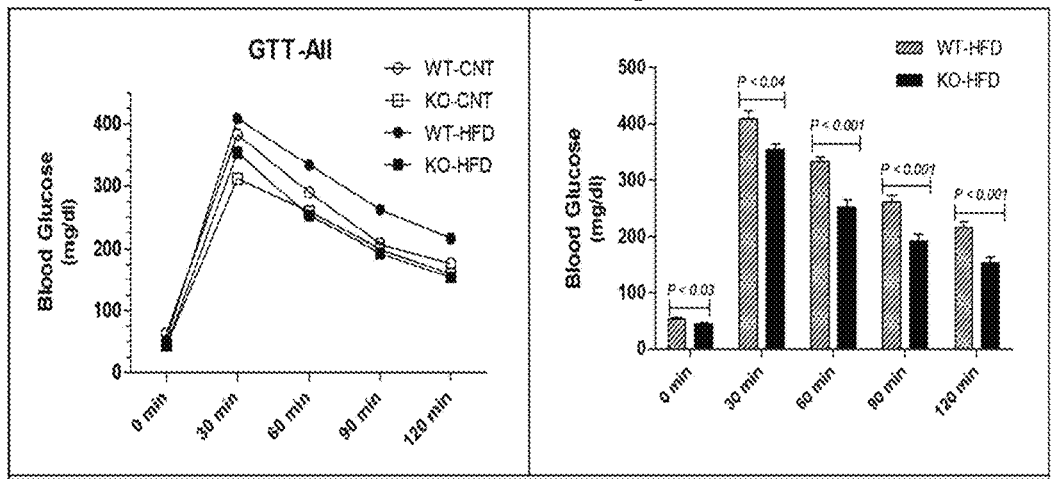
Fig. 10: Evaluation of Glucose Tolerance in Wild Type (WT) and P2Y$_2$ knockout (KO) Mice fed High-Fat Diet (HFD) with ad libitum Access to Food and Drinking Water. GTT test done during 14$^{th}$ week.
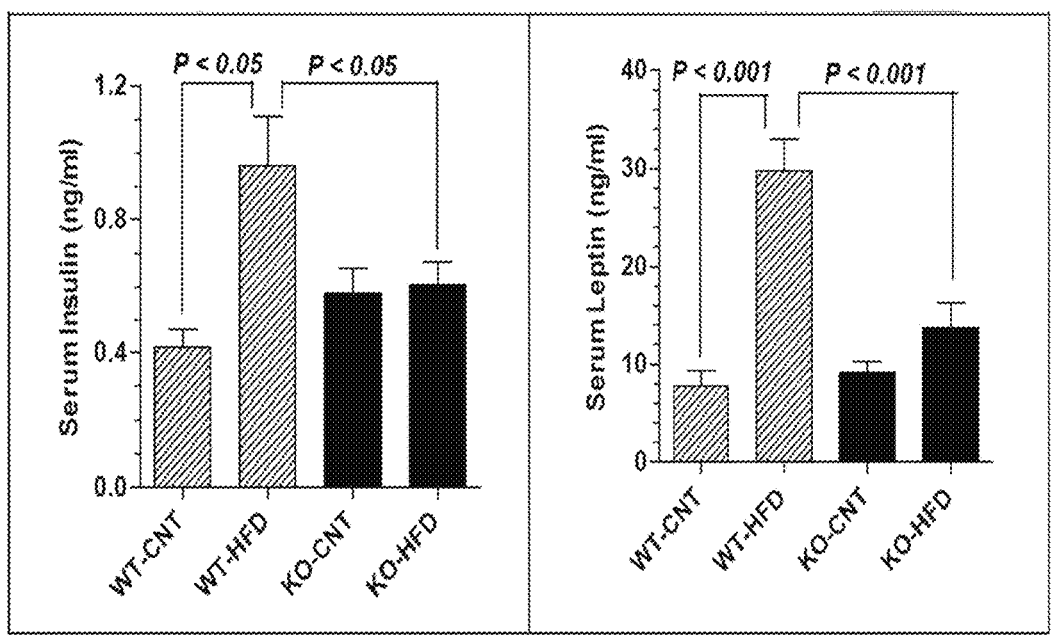
Fig. 11: Serum Insulin and Leptin Levels in Wild Type (WT) and P2Y$_2$ knockout (KO) Mice fed Regular Diet (CNT) or High-Fat Diet (HFD) with ad libitum Access to Food and Drinking Water for 16 weeks.

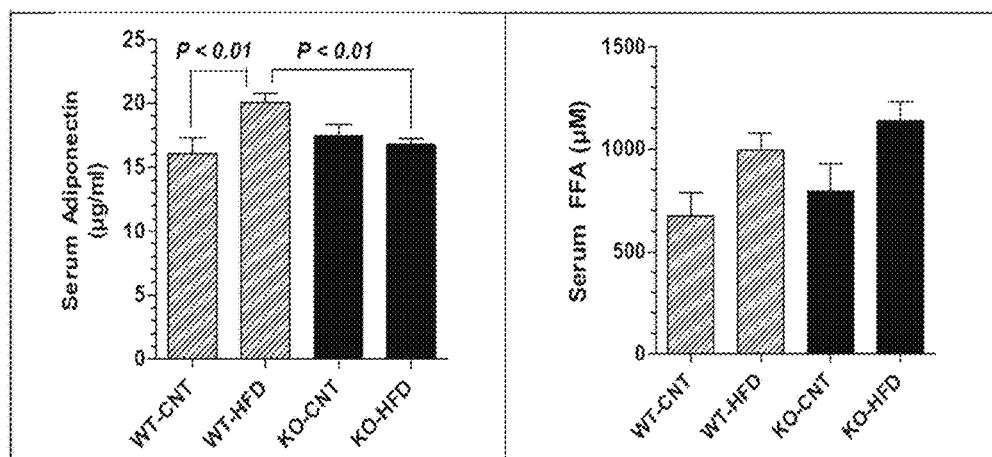

Fig. 12: Serum Adiponectin and Free Fatty Acid (FFA) Levels in Wild Type (WT) and P2Y$_2$ knockout (KO) Mice fed Regular Diet (CNT) or High-Fat Diet (HFD) with ad libitum Access to Food and Drinking Water for 16 weeks.

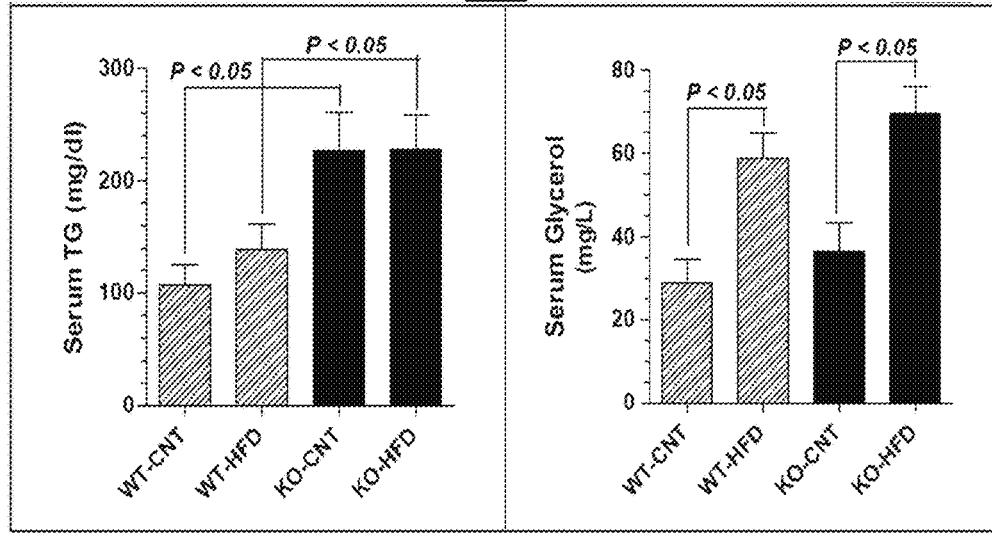

Fig. 13: Serum Triglycerides (TG) and Glycerol Levels in Wild Type (WT) and P2Y$_2$ knockout (KO) Mice fed Regular Diet (CNT) or High-Fat Diet (HFD) with ad libitum Access to Food and Drinking Water for 16 weeks.

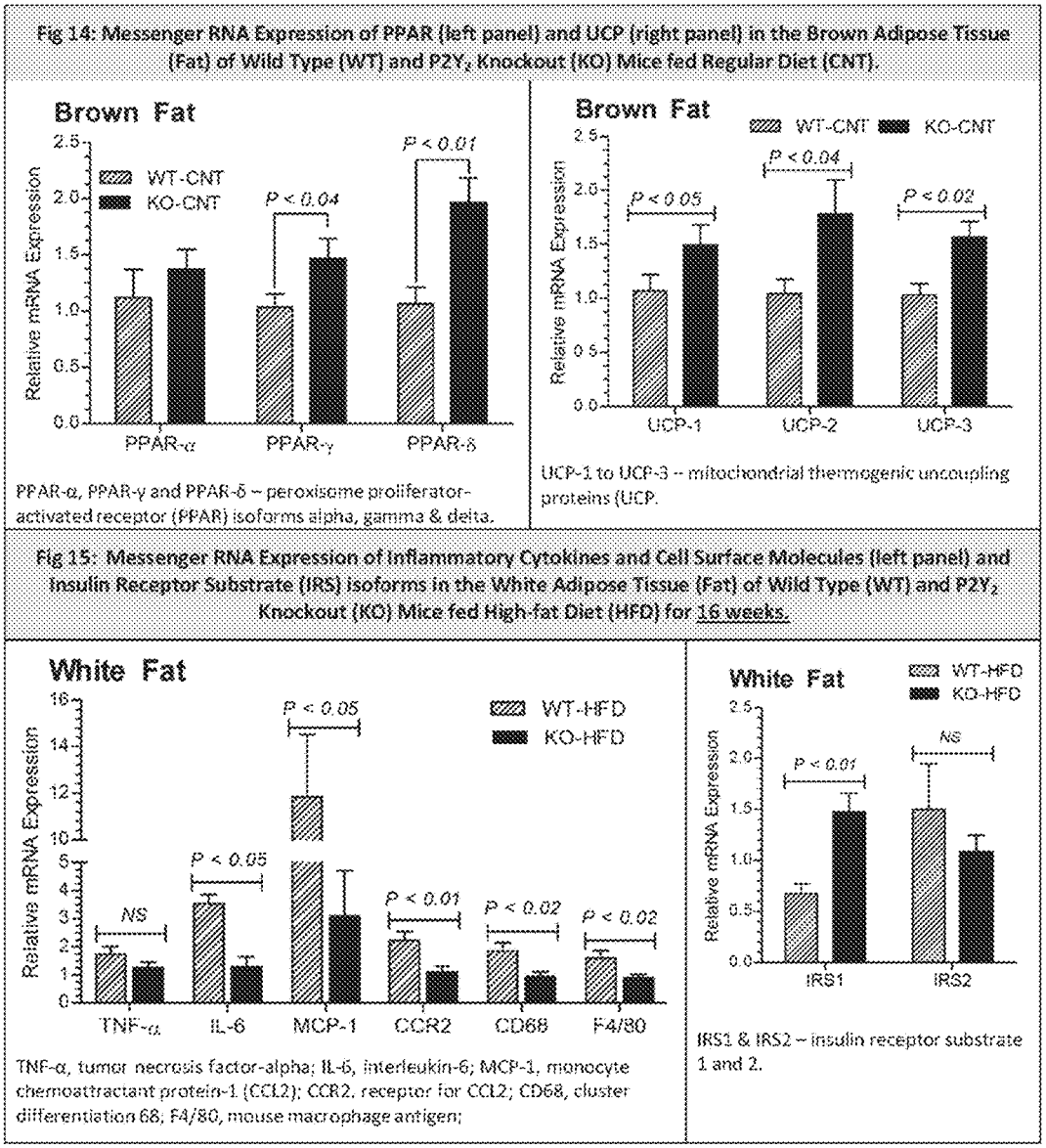

COMPOSITION AND METHODS FOR THE PREVENTION AND TREATMENT OF DIET-INDUCED OBESITY

CROSS-REFERENCE TO RELATED APPLICATION

This application is a National Stage filing under 35 U.S.C. § 371 of International Application PCT/US2013/066932 filed Oct. 25, 2013 which claims priority to U.S. Provisional Patent Application No. 61/795,815, filed Oct. 25, 2012. The entirety of each application is hereby incorporated herein by reference.

GOVERNMENT RIGHTS

The present invention was made with government support under Department of Veterans Affairs Merit Review Program, Grant No. BLRD 000591, and the facilities and resources at the VA Salt Lake City Health Care System. The Government has certain rights to this invention.

FIELD OF THE INVENTION

Blunting the activity of the $P2Y_2$ receptor results in a resistance to diet-induced obesity, an increased metabolic activity, and a better glucose tolerance. Therefore, compounds that inhibit the puringeric $P2Y_2$ receptor are useful for treating diet-induced obesity and metabolic disorders associated therewith, such as diabetes mellitus.

BACKGROUND OF THE INVENTION

Obesity is one of the major public health problems of the 21st century with significant consequences on health of the individuals and impact on the national economies. The most common cause of obesity is diet-induced, i.e., consumption of more calories than one can metabolize. In view of the rapidly growing number of obese people throughout the world, the global market for anti-obesity drugs is estimated to reach $3.4 billion by 2016. However, currently available drugs for the treatment of obesity have significant limitations in terms of safety, efficacy or both. Thus, there is a high unmet need for safe and efficacious medications for the prevention or treatment of obesity. This invention discloses a potential drug target for the treatment of diet-induced overweight or obesity. This approach involves increasing the metabolism of consumed excess calories, which may prove to be safer or tolerable than the other two approaches, namely suppression of the appetite or interfering with the absorption of fat in the intestines. It is possible to develop orally effective chemical compounds that selectively act at the disclosed target as potential anti-obesity drugs.

According to the World Health Organization, a Body Mass Index (BMI)>25 is overweight, and a BMI>30 is obesity. Overweight and obesity are no more the problems of high-income countries of the world. They are rapidly rising in low- and middle-income countries.

In 2008 the World Health Organization estimated that globally more than 1.4 billion adults were overweight; and the 2010 estimates showed that more than 40 million children under five years are overweight. Overweight and obesity are the fifth leading risk for global deaths, accounting for 2.8 million deaths each year. In fact, overweight and obesity are linked to more deaths worldwide than underweight.

Raised BMI is a major risk factor for cardiovascular and musculoskeletal disorders, and certain types of cancers, such as breast and colon cancers. In fact, 44% of the diabetic burden, 23% of the ischemic heart disease burden and between 7% and 14% of certain cancer burdens are attributable to overweight and obesity.

The global economic burden of overweight and obesity are not well established. But the numbers are more accurately available for the United States. Over the past 50 years the prevalence of obesity in the USA has almost tripled from 13% to 34%, with the percentage of Americans who are extremely or "morbidly" obese rising from 0.9 to 6. The estimated annual medical costs due to obesity are about $190 billion. The indirect costs due to overweight and obesity are also sky rocketing. For example, it is estimated that airlines incur about $5 billion annually for additional jet fuel needed to fly obese or heavier people as compared to the fuel needed to fly the same number of people based on the body weights prevalent in 1960s. Automobiles also consume extra gasoline amounting to about $4 billion to transport heavier people in the USA. The annual costs due to absenteeism among over weight and obese people are also very high. In fact, according to a study, the costs of obesity exceed those of smoking.

According to the World Health Organization, the fundamental cause of obesity and overweight is energy imbalance between calories consumed and calories expended. In recent decades globally there has been an increase in caloric intake and a decrease in the physical activity, driving the incidence of obesity high. Although supportive environments and communities resulting in consumption of healthy foods and regular physical activity are the best to prevent overweight and obesity, these do not happen often, in part because of the complex nature of modern day living.

Currently used modalities as well as the pipeline drugs for the prevention and/or treatment of obesity fall into the following three categories: (1) drugs that suppress appetite by acting on the brain (e.g., sibutramine (i.e., Reductil® and/or Meridia®); (2) drugs that boost body's metabolic rate (e.g., cannaboid receptor antagonists and Metformin); and (3) drugs that interfere with the body's ability to absorb specific nutrients in food, such as fat (e.g., Orlistat®, Xenical®, and/or Alli®).

Drugs that suppress the appetite by acting on the brain have severe side effects which are neurological and/or psychological in nature. For example, these drugs carry a risk of high blood pressure, faster heart rate, palpitation, restlessness, agitation, insomnia etc. Due to these limitations, drugs that suppress appetite have been withdrawn from the market by the FDA and approval of newer drugs has been made more stringent. Drugs that increase the body's metabolic rate have their own limitations, such as lack of consistent effect resulting in sustained loss of weight. Drugs that block absorption of dietary fat, cause oily stools (steatorrhea), abdominal pain and flatulence.

In view of the side effects with these therapies, combination therapies that target more than one pathway have been developed. However, these also have severe side effects and limitations, despite their efficacy in short-term treatment. Accordingly, there is a high unmet need for safe and effective medications for the prevention or treatment of overweight and obesity, which is expected to drive the anti-obesity market growth in the future. The invention described herein seeks to meet this need.

SUMMARY OF THE INVENTION

Provided herein are methods for selectively blocking the activity of the P2Y2 purinergic receptor for the prevention and/or treatment of diet-induced overweight or obesity. It was discovered that the genetic deletion of P2Y2 receptor results in resistance to the development of high-fat diet-induced obesity and the associated physical and molecular alterations in mice. The results described also suggest that the observed resistance of the P2Y2 receptor in knockout mice was not due to reduced consumption of high-fat diet or lack of absorption of fat in the intestines, but may be due to the ability of the knockout mice to metabolize or "burn" the extra calories consumed in the diet more efficiently than the wild type mice. Accordingly, targeting P2Y2 receptor with specific pharmacological agents or drugs is a safe approach to prevent or treat diet-induced overweight or obesity.

In various embodiments, provided herein are methods for treating or preventing diet-induced obesity in a subject by administering an agent that blunts the expression or activity of the $P2Y_2$ receptor in the subject.

In some specific embodiments, the agent is a fusion protein or an agent that inhibits the $P2Y_2$ receptor. In specific embodiments, the agent is a selective $P2Y_2$ receptor antagonist, including but not limited to a non-nucleic acid small organic molecule.

In other embodiments, the agent is an oligonucleotide. In specific embodiments, the oligonucleotide is an antisense oligonucleotide, a ribozyme or an inhibitory RNA, including but not limited to a small inhibitory RNA (siRNA).

In other embodiments, provided herein are methods for increasing energy metabolism in a cell by contacting the cell with an agent that blunts the expression or activity of a $P2Y_2$ receptor, thereby increasing the metabolism in the cell. In specific embodiments, the cell is an adipocyte cell.

In specific embodiments, the agent is a fusion protein, polypeptide, a small non-nucleic acid organic molecule, a small inorganic molecule or an oligonucleotide, including but not limited to an antibody, an antisense oligonucleotide, a ribozyme, or an inhibitory RNA, including but not limited to a small inhibitory RNA (siRNA).

Also provided herein are methods for increasing energy metabolism in an adipocyte cell in a subject that is at risk for or suffering from a disorder related to glucose metabolism, the method comprising administering to the subject an agent that inhibits expression or activity of a $P2Y_2$ receptor, thereby increasing the metabolism in the cell.

In various specific embodiments, the agent is a polypeptide, a small non-nucleic acid organic molecule, a small inorganic molecule, an antibody, an antisense oligonucleotide, a ribozyme or an inhibitory RNA, including but not limited to a small inhibitory RNA (siRNA).

Provided herein is also a method for identifying a candidate agent that modulates expression or activity of the $P2Y_2$ receptor, comprising: (a) providing a sample comprising the $P2Y_2$ polypeptide or a nucleic acid encoding the polypeptide; (b) contacting the sample with a test compound under conditions in which the polypeptide is active, the nucleic acid is expressed, or both; (c) evaluating expression or activity of the $P2Y_2$ polypeptide in the sample; and (d) comparing the expression or activity of the $P2Y_2$ polypeptide of (c) to the expression or activity of the $P2Y_2$ polypeptide in a control sample lacking the test compound, wherein a change in the $P2Y_2$ polypeptide expression or activity indicates that the test compound is a candidate agent that can modulate the expression or activity of the $P2Y_2$ polypeptide.

In various specific embodiments, the candidate agent selectively inhibits the $P2Y_2$ receptor or is a fusion protein Other features and advantages of the present invention will become more readily apparent to those of ordinary skill in the art after reviewing the following detailed description and accompanying drawings.

BRIEF DESCRIPTION OF THE DRAWINGS

The details of the present invention may be gleaned in part by study of the accompanying drawings, in which:

FIG. 1 illustrates the changes in the body weights and P2Y2 knockout and wild-type mice fed regular diet or high-fat diet for 16 weeks.

FIG. 2 shows the size of one of the highest weighing wild-type mouse with an average weighing P2Y2 knockout mouse from the high-fat diet groups.

FIG. 3A illustrates the food intake (g/day or g/g body weight) of the mice after 4 weeks of the Experimental Period.

FIG. 3B illustrates the food intake (g/day or g/g body weight) of the mice after 12 weeks of the Experimental Period.

FIG. 4A illustrates the water intake (ml/day or ml/g body weight) of the mice after 4 weeks of the Experimental Period.

FIG. 4B illustrates the water intake (ml/day or ml/g body weight) of the mice after 12 weeks of the Experimental Period.

FIG. 5A illustrates the urine output (ml/g body weight) and urine osmolality (mOsm/Kg) after 4 weeks of the Experimental Period.

FIG. 5B illustrates the urine output (ml/g body weight) and urine osmolality (mOsm/Kg) after 12 weeks of the Experimental Period.

FIG. 6A illustrates the appearance of abdominal fat in a (a) wild type mouse on a regular diet, (b) wild type mouse on a high-fat diet, and (c) P2Y2 knockout mouse on a high-fat diet, at the time of euthanasia.

FIG. 6B is a representative picture of white fat from a high-fat diet wild type mouse (left) and knockout mouse (right).

FIG. 6C is a representative picture of brown fat from a high-fat diet wild type mouse (left) and knockout mouse (right).

FIG. 7A illustrates the terminal weight of white adipose tissue (mg and mg/20 g body weight).

FIG. 7B illustrates the terminal weight of brown adipose tissue (mg and mg/20 g body weight).

FIG. 8 illustrates the terminal weight of the liver and kidney (mg/20 g body weight) in the mice after 16 weeks of the Experimental Period.

FIG. 9 provides illustrative samples of the fecal matter in high-fat diet fed wild type mice (left) and knockout mice (right) during the 16 week Experimental Period.

FIG. 10 provides the results of a Glucose Tolerance Test during the $14^{th}$ week of the Experimental Period.

FIG. 11 provides the results of a Serum Insulin assay (left) and a Serum Leptin assay (right) after 16 weeks of the Experimental Period.

FIG. 12 provides the results of a Serum Adiponectin assay (left) and a Serum Free Fatty Acid assay (right) after 16 weeks of the Experimental Period.

FIG. 13 provides the results of a Serum Triglycerides assay (left) and a Serum Glycerol assay (right) after 16 weeks of the Experimental Period.

FIG. 14 provides Messenger RNA Expression level of PPAR in the Brown Fat (left) and the Messenger RNA Expression level of UCP in the Brown Fat (right).

FIG. 15 provides the Messenger RNA Expression level of Inflammatory Cytokines and Cell Surface Molecules (TNF-α, IL-6, MCP-1, CCR2, CD68, F4/80) in the White Fat (left) and the Messenger RNA Expression level of Insulin Receptor Substrate Isoforms (IRS 1, IRS 2) the White Fat (right).

DETAILED DESCRIPTION OF ILLUSTRATIVE EMBODIMENTS

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

As shown herein, it was discovered that mice with genetic deletion of P2Y2 receptor consume the same amount of high-fat diet as their syngeneic wild type mice do, and do not excrete fatty stools (steatorrhea), yet do not become obese. This suggests that P2Y2 receptor is a potential target for the development of efficacious and safer anti-obesity drugs. One possible reason for this phenomenon is that purinergic P2Y2 receptor is involved in energy metabolism and so its genetic deletion significantly protects against high-fat diet-induced obesity. Accordingly, purinergic antagonism may prove to be a very advantageous invention over the current state-of-the-art.

This is further supported by the fact that one promising line of future anti-obesity drugs is based on the development of ribonucleic acid interference (RNAi) to silence RIP140 gene, a nuclear co-repressor that regulates fat accumulation. This line of drug development was prompted by the observation that mice with genetic deletion of RIP140 exhibit a lean profile throughout their life, and are resistant to diet-induced obesity, and show an enhanced metabolic rate. CytRx Corporation is currently developing RNAi therapeutics against this drug target (RIP140) for the treatment of obesity and type 2 diabetes. Conversely, disruption of the molecular interaction between SMRT, a nuclear hormone receptor co-repressor and its receptor partner leads to increased adiposity and decreased metabolic rate.

The novel findings described herein open the possibility to develop an entirely new line of drugs that target the molecular interactions between G protein-coupled receptors and their downstream regulatory effectors to prevent or treat diet-induced obesity. Thanks to the availability of gene knockout mice that carried these molecular disruptions in vivo throughout their lifespan, researchers are able to assess the efficacy and safety of this promising approach in live mice.

As discussed in detail herein, it was discovered that genetic deletion of P2Y2 receptor causes resistance to diet-induced obesity. The data indicates that this effect is likely related to increased metabolic rate and the effect is associated with better glucose tolerance as well as a sign of better balance between energy intake and expenditure.

The invention described herein has potential practical and commercial applications to develop a new line of anti-obesity drugs that are safe and efficacious. This can be achieved by either designing and developing P2Y2 receptor selective antagonists (chemical molecules) or RNAi to silence the P2Y2 receptor gene.

EXAMPLES

Example 1: Mice that are Genetically Deficient in P2Y2 Receptor

A bench prototype was generated in mice that are genetically deficient in P2Y2 receptor. These mutant mice apparently do not suffer from diseases, have no pathological lesions and live healthy. Although one study showed that these mice develop salt-resistant hypertension, the rise in blood pressure was modest, and these mice do not develop complications of hypertension, such as kidney disease. See., Rieg et al., 2007, FASEB J 21:3717-3726.

Hence, targeting purinergic signaling for the treatment of obesity is relatively safe as compared to the current state-of-the-art. Any potential increase in blood pressure can be effectively controlled with combination therapy.

Example 2: Wild Type and P2Y2 Receptor Knockout Study

A study was performed on wild type and P2Y2 receptor knockout mice (both in B6D2 genetic background). Breeders of these mice were originally obtained from Dr. Beverly Koller of the University of North Carolina at Chapel Hill, Chapel Hill, N.C.

Obesity is associated with deranged sodium homeostasis leading to hypertension among other pathologies. Hence, this high-fat diet study was conceived to examine the role of P2Y2 receptor in obesity-induced alterations in water and sodium handling by the kidney, leading to hypertension. Since kidney is one of the vital organs affected by obesity, we posited that any new information obtained may help us to address more complex questions, such as the course of lithium-induced nephrogenic diabetes insipidus in obese patients and the effect of lack of purinergic signaling. However, during the study we observed that P2Y2 receptor knockout mice were resistant to the diet-induced obesity, which forms the basis for this invention.

Experimental Study Parameters

Breeding colonies were established in the Veterinary Medical Unit (VMU) of the VA Salt Lake City Health Care System. Mice bred were identified by Polymerase Chain Reaction ("PCR") on DNA extracted from the tail clippings, and all mice were tracked by implanting microchip transponders under the skin. Age matched adult wild type and P2Y2 receptor knockout (KO) mice were randomly divided into two sub-groups for each genotype and were fed regular rodent chow (10% of total energy as fat) or high-fat diet (60% or total energy as fat) for 16 weeks as shown below. The high-fat diet was purchased from the Research Diets, Inc. (New Brunswick, N.J.).

| Wild Type Mice | | $P2Y_2$ Receptor Knockout Mice | |
|---|---|---|---|
| Regular Diet | High-Fat Diet | Regular Diet | High-Fat Diet |
| N = 6 | N = 14 | N = 6 | N = 14 |

All mice had free access to drinking water throughout the experimental period. Food intake and body weights were monitored on regular basis. Twenty-four hour urine samples were collected periodically by placing the mice in metabolic cages with free access to food and drinking water. Feces samples of all groups of mice were collected periodically. During the 14$^{th}$ week tolerance of the mice to an acute load of glucose was assessed by carrying out glucose tolerance test ("GTT"). All mice were euthanized at the end of the experimental period and samples of blood, liver, kidney, pancreas, spleen and whole white and brown adipose tissues were collected for analysis in the laboratory.

The GTT tests were performed as described by Takahashi et al (2011). Briefly, after a fasting period of about 12 hours, the mice received an intraperitoneal injection of sterile glucose solution (1.5 g/kg body wt.). Tiny droplets of blood (~5 µl) were obtained in conscious mice by gently pricking the dorsal pedal vein with a fine needle. Using these droplets, blood glucose levels were determined with a clinical glucometer. Blood samples were collected prior to (0 min), and 30, 60, 90 and 120 min after intraperitoneal injection of glucose solution.

Twenty-four hour urine output was recorded, and the osmolalities of clear urine samples were determined by vapor pressure method on an osmometer (Wescor, Logan, Utah). Insulin, leptin, adiponectin, triglycerides and glycerol levels in the serum samples were determined by using commercial ELISA or EIA kits (Crystal Chem, Inc., Downers Grove, Ill. or Cayman Chemical Co., Ann Arbor, Mich.). Weights of total brown or white adipose tissues were determined for each mouse. Total liver and kidney weights were also determined.

Liver tissue samples were analyzed for metabolic changes in the University of Utah Metabolomic Core Facility using gas chromatography-mass spectrometry (GC-MS). For this analysis, about 20 mg of liver tissue from each mouse (N=6 mice/group) was used. The liver tissue was flash frozen in liquid nitrogen at the time of euthanasia and then stored at −80° C. In the core facility, the tissue was mechanically disrupted using a bead mill, and metabolites were extracted by a solvent. After evaporating the solvent, the dried samples were suspended in O-methoxylamine hydrochloride (MOX) and further processed for GC-MS. GC-MS data was collected using MassLynx 4.1 software (Waters).

A two-step process was employed for data analysis, a targeted followed by non-targeted analysis. For the targeted approach known metabolites were identified and their peak areas were recorded using QuanLynx. For the non-targeted approach peak picking and analysis was performed using MarkerLynx. Principle components analysis (PCA) and partial least squares-discriminate analysis (PLS-DA) was performed using SIMCA-P 12.0 (Umetrics, Kinnelon, N.J.). Metabolite identity was established using a combination of an in-house metabolite library developed using pure standards and the commercially available NIST library. Not all metabolites were observed using GC-MS.

Quantitative data are presented as mean±sem. Comparisons among the means of multiple groups were made by one-way analysis of variance (ANOVA), followed by the assessment of statistical significance by Tukey-Kramer Multiple Comparison test or Boneferroni test for selected pairs. Differences between the means of two groups were determined by unpaired t-test or Mann-Whitney nonparametric method. P values less than 0.05 were considered significant. GraphPad Instat® software (GraphPad Software, Inc., La Jolla, Calif.) was used for statistical analysis.

Study Results

FIG. 1 illustrates the changes in the body weights in (WT) and P2Y2 knockout (KO) mice fed regular diet or high-fat diet for 16 weeks. As shown in FIG. 1A, the WT mice had modestly, but significantly higher body weights even on day 0 as compared to the age-matched KO mice. Following high-fat diet feeding, the body weight or WT mice steadily increased starting at 2 weeks. In contrast, body weights of high-fat diet fed KO mice essentially remained similar to the regular diet-fed KO mice throughout the study period. FIG. 1B and FIG. 1C show the terminal (16 weeks) body weights of the high-fat diet fed WT vs. high-fat diet fed KO mice. The differences between these two groups are striking when analyzed as weights of individual mice using scattergraph (FIG. 1B) or as box plots (FIG. 1C).

FIG. 2 shows a picture of mice to compare the size of one of the highest weighing WT mice from the high-fat diet group (WT-HFD) with an average weighing KO mouse from the high-fat diet group (KO-HFD). In order to exclude the possibility that the differences observed in body weights of the WT and KO mice was due to differences in their food and/or water intake, the food and water intake of the mice at two different time points was determined (see below).

FIG. 3A shows food intake as g/day/mouse after 4 weeks. As shown in this figure, the high-fat diet fed WT mice consumed significantly less amount of food as compared to the regular diet fed WT mice. However, there was no difference in the food intake between the WT or KO mice when high-fat diet was fed to them.

FIG. 3B shows food intake in high-fat diet fed WT or KO mice after 12 weeks. The left panel presents the data as g/day/mouse, whereas the right panel shows the data as g/g body weight per day. Notably, at this time point the KO mice were consuming significantly higher amount of food, despite the fact that their body weights were significantly lower as compared to the body weights of the high-fat diet fed WT mice (see, FIG. 1). Thus, the observed lack of gain in the body weight in high-fat diet fed KO mice was not due to consumption of lesser amount of food. In fact, food consumption in these mice is relatively higher when normalized to the body weight.

FIG. 4A shows water intake as ml/day/mouse after 4 weeks. Although there were no significant differences between the genotypes, high-fat diet significantly reduced water intake in both genotypes. FIG. 4B shows water intake in high-fat diet fed WT and KO mice after 12 weeks. The left panel presents data as ml/day/mouse, whereas the right panel shows data as ml/g body weight per day. Similar to the food consumption, the KO mice were drinking significantly higher amount of water relative to their body weight, despite the fact that their body weights were significantly low as compared to the body weights of the high-fat diet fed WT mice (see, FIG. 1).

FIG. 5A shows urine output and urine osmolality after 4 weeks in WT and KO mice fed regular or high-fat diets. As shown in the left panel, high-fat diet caused significant decrease in urine output in both genotypes. However, high-fat diet did not have any effect on the urine osmolality in WT or KO mice. FIG. 5B shows urine output and urine osmolality in high-fat diet fed WT and KO mice after 12 weeks. Interestingly at this time point the urine output when expressed as mug body wt/day was modest, but significantly higher in the KO mice (left panel). However, no differences were noted in urine osmolality between these two groups after 12 weeks.

FIG. 6A shows representative pictures of the appearance of abdominal fat at the time of euthanasia. Panel 6Aa shows the appearance of normal content and disposition of abdominal fat in a WT mouse fed regular diet, which is similar to KO mice fed a regular diet (not shown here). In contrast, high-fat diet fed WT mice have much higher amounts of abdominal fat (FIG. 6Ab) as compared to the high-fat diet fed KO mice (FIG. 6Ac).

In mammals, fat or adipose tissue exists in two distinctive forms—the white and brown adipose tissues. White adipose tissue is a storage form of energy and accumulates excessive calories consumed as fat droplets, usually found around the abdominal wall or the belly. White adipose tissue burns slowly, and is linked to the risk for diabetes and heart diseases. Conversely, the brown fat, which is rich in mitochondria and capillaries (hence the color), burns calories to generate heat. Brown fat is abundant in newborns and hibernating mammals, whereas the white fat is abundant in adults. FIG. 6B and FIG. 6C are representative pictures of white or brown fat obtained from the high-fat diet fed WT or KO mice. The difference in the masses of these two types of tissues between the genotypes was quite obvious.

FIG. 7A shows the terminal weights of white adipose tissue in the WT and KO mice fed regular or high-fat diet. As shown, the WT mice fed high-fat diet had a 2 to 3-fold higher amount of white fat as compared to the regular diet fed WT mice, depending on whether the fat content was expressed as mg/mouse or mg/20 g body weight. On the other hand, the high-fat diet feeding had no significant effect on the white adipose tissue in the KO mice. FIG. 7B shows the terminal weights of brown adipose tissue in WT and KO mice fed high-fat diet. Similar to the white adipose tissue, high-fat diet feeding had a significant effect on brown adipose tissue only in the WT mice.

Since the liver and kidney are two vital organs affected by obesity, their weights were recorded as a function of body weight at the time of euthanasia. As shown in FIG. 8, in high-fat diet fed WT mice the weights of both liver and the kidney were significantly low when adjusted for the body weight. In contrast, a high-fat diet did not have any effect on the weights of the liver and kidney in KO mice.

If the apparent resistance of the KO mice to high-fat diet induced increase in body weight and accumulation of body fat is due to defective absorption of fat in the intestines, then one would expect steatorrhea in these mice. Steatorrhea is a condition where the feces contain partially digested fat as oil. The feces are not well formed, and have an oily appearance and foul smell. Hence, the fecal matter in the high-fat diet fed WT and KO mice was monitored. FIG. 9 shows representative profiles of the fecal matter in high-fat diet fed wild type (WT-HFD) and knockout (KO-HFD) mice collected during the last week of experimental period (16 weeks). As illustrated in this figure, both WT and KO mice fed high-fat diet have well-formed, and non-oily fecal matter. These observations rule out the possibility of lack of absorption of fat in the intestines in KO mice.

Glucose tolerance or the ability to metabolize a load of glucose is impaired in obese subjects. And obesity is a known risk factor for the development of type II diabetes, where the subjects develop resistance to insulin and thus cannot metabolize glucose efficiently, despite high blood insulin levels. To examine whether the high-fat diet induced increase in body weight in the wild type mice is associated with glucose intolerance, a Glucose Tolerance Test (GTT) using a standard protocol was performed.

FIG. 10 shows the results of the GTT in different groups of mice. As shown in the left panel of FIG. 10, at 30 min after an acute load of glucose, the high-fat diet fed WT mice showed the highest blood level of glucose, about 400 mg/dl. The corresponding blood glucose level in high-fat diet fed KO mice was significantly low. In fact at all the time points following an acute glucose load, the high-fat diet fed KO mice had significantly lower blood glucose levels as compared to the high-fat diet fed WT mice (FIG. 10, right panel).

Notably, the baseline (0 min) blood glucose levels in the WT mice were modest, but significantly elevated as compared to the KO mice (FIG. 10, right panel). Furthermore, at 30 min time point following an acute load of glucose, the differences among the four groups were very obvious, with the two WT groups having higher blood glucose levels as compared to the two KO groups. Similar to the high-fat diet fed WT and KO mice, the differences in blood glucose levels between the regular diet fed WT and KO mice were also wide apart at 30 min time point, indicating that KO mice are inherently efficient in metabolizing a load of glucose faster.

Insulin, released from the beta-cells of islets of Langerhans in the pancreas in response to increasing blood glucose levels (e.g., following a meal), is the key hormone in regulating the blood glucose levels by inducing uptake of glucose by cells and its subsequent metabolism. In type II diabetes, the cells develop resistance to the action of insulin with the result the subjects have both high blood glucose and high blood insulin levels. The left panel of FIG. 11 shows terminal serum insulin levels in the blood samples collected at the time of euthanasia. As illustrated in this figure, following high-fat diet feeding for 16 weeks, the WT mice had more than 2-fold increase in serum insulin. The insulin levels in the KO mice were not affected by high-fat diet feeding. These results correlate well with the pattern of GTT results obtained.

Leptin is a peptide hormone elaborated mainly by white adipose tissue, although brown adipose tissue and other organs also produce leptin. The levels of circulating leptin are proportional to the total amount of the fat in the body. In general, leptin is considered to play a key role in regulating energy intake and energy expenditure, including appetite and metabolism. Leptin acts on the hypothalamus and inhibits appetite. Hence, the absence of leptin leads to uncontrolled food intake resulting in obesity, e.g., ob/ob mutant mice that lack leptin.

When these mutant mice are treated with leptin injections, they lose excess body fat and return to normal body weight. However, despite these properties of leptin, obese subjects often develop resistance to leptin so their appetite is not reduced by high circulating leptin levels. This is because of leptin desensitization due to high circulating leptin levels in obese subjects. In view of this, serum levels of leptin in the mice were determined. As shown in the right panel of FIG. 11, high-fat diet feeding for 16 weeks caused more than a 3-fold increase in the serum leptin levels in WT mice. The increase in serum leptin levels in high-fat diet fed KO mice was modest.

Adiponectin is a protein hormone produced exclusively from adipose tissue (and also from placenta during pregnancy). Adiponectin modulates a number of metabolic functions, such as glucose metabolism and fatty acid catabolism. Adiponectin also plays roles in the suppression of metabolic derangements, such as those occurring due to type II diabetes mellitus, obesity, atherosclerosis, as well as others. In general, adiponectin is considered as an independent risk factor for metabolic syndrome. Similar to leptin, the weight reducing effects of adiponectin are mediated via brain. In view of this, the serum adiponectin levels in the blood samples collected was determined at the time of euthanasia, i.e., after 16 weeks of feeding the respective diets.

As shown in FIG. 12 left panel, the serum adiponectin levels are modestly, but significantly elevated in high-fat diet fed WT mice, but not in KO mice. The increase in serum adiponectin in the WT mice may be due to higher fat content in the body, and also in response to the increase in the body weight. However, similar to higher serum leptin levels in these mice, the higher adiponectin levels did not counter the high-fat diet-induced increase in body weight in WT mice. Since adiponectin is involved in fatty acid catabolism, the serum free fatty acids (FFA; FIG. 12, right panel), serum triglycerides (TG; FIG. 13, left panel) and serum glycerol (FIG. 13, right panel) were determined. As shown, the serum FFA levels were not significantly different among the four groups of mice, although high-fat diet had a tendency for higher levels of serum FFA in both genotypes. Interestingly, serum TG levels were significantly higher in KO mice as compared to the WT mice, irrespective of the dietary regimen, and dietary regimen itself did not have any effect in either genotype. In contrast, a high-fat diet triggered significantly higher (about 2-fold) serum glycerol levels in both genotypes.

Further insights into the metabolic profiles of the WT and KO mice and the effect of high-fat diet feeding, were obtained by performing a metabolomics analysis of the liver tissue. Table 1 below provides the data obtained for 23 carbohydrate metabolites, 20 protein metabolites, 22 lipid metabolites and 5 nucleic acid metabolites.

TABLE 1

Metabolomic Analysis of Liver Tissue by GC-MS
GC-MS data presented here are in arbitrary units and expressed as mean ± sem
Metabolites shown in orange background with an asterisk on the right end of the line have interesting or significant trends with respect to genotype or dietary regimen or both.

|  | WT-CNT | WT-HFD | KO-CNT | KO-HFD |  |
|---|---|---|---|---|---|
| Carbohydrate Metabolites | | | | | |
| Lactic Acid | 687 ± 89 | 556 ± 59 | 559 ± 59 | 585 ± 64 | |
| Pyruvic Acid | 159 ± 34 | 129 ± 9 | 110 ± 9 | 118 ± 6 | |
| Glycerol | 1.26 ± 1.00 | 0.69 ± 0.06 | 3.82 ± 0.24 | 2.85 ± 0.78 | * |
| Glyceric Acid | 558 ± 44 | 763 ± 79 | 475 ± 32 | 941 ± 49 | * |
| Citric Acid | 35.3 ± 3.1 | 34.2 ± 4.4 | 34.4 ± 3.8 | 37.0 ± 5.9 | |
| Aconitic Acid | 7.08 ± 1.38 | 3.08 ± 0.74 | 3.12 ± 0.21 | 2.85 ± 0.43 | |
| Isocitric Acid | 6.03 ± 1.25 | 9.65 ± 3.94 | 5.06 ± 0.21 | 5.58 ± 0.67 | |
| 2-Ketoglutaric Acid | 1.99 ± 0.57 | 1.97 ± 0.31 | 1.08 ± 0.37 | 1.61 ± 0.24 | |
| Succinic Acid | 2463 ± 291 | 2657 ± 293 | 2402 ± 332 | 3130 ± 340 | |
| Fumaric Acid | 355 ± 14 | 327 ± 45 | 279 ± 50 | 330 ± 36 | |
| Malic Acid | 709 ± 49 | 753 ± 110 | 558 ± 73 | 819 ± 100 | |
| 2-Hydroxyglutarate | 4.06 ± 0.34 | 4.29 ± 0.48 | 1.72 ± 0.44 | 3.09 ± 0.39 | |
| 2-Aminoadipic Acid | 5.70 ± 1.02 | 9.11 ± 1.54 | 7.84 ± 1.85 | 14.72 ± 4.25 | * |
| Glucose | 21885 ± 853 | 22570 ± 1575 | 20706 ± 587 | 20302 ± 253 | |
| Fructose | 466 ± 62 | 536 ± 60 | 442 ± 47 | 535 ± 45 | |
| Ribose | 0.287 ± 0.019 | 0.395 ± 0.079 | 0.222 ± 0.011 | 0.321 ± 0.094 | * |
| Galactose or isomer | 2605 ± 283 | 1942 ± 112 | 1994 ± 166 | 1571 ± 49 | * |
| Glucose-1-Phosphate | 204 ± 22 | 194 ± 18 | 338 ± 27 | 214 ± 25 | * |
| Glucose-6-Phosphate | 1009 ± 106 | 1025 ± 161 | 1922 ± 142 | 1285 ± 149 | * |
| Sorbitol | 19.9 ± 3.6 | 12.5 ± 1.1 | 22.2 ± 4.0 | 6.5 ± 1.0 | * |
| Galacitol | 289 ± 55 | 337 ± 15 | 245 ± 40 | 348 ± 52 | |
| Disaccharide | 5126 ± 1454 | 5581 ± 743 | 3866 ± 859 | 1474 ± 314 | * |
| Xylulose-5-monophosphate | 24.3 ± 1.9 | 20.1 ± 3.5 | 22.5 ± 1.5 | 23.2 ± 1.6 | |
| Protein Metabolites | | | | | |
| Lysine | 40.3 ± 16.3 | 41.2 ± 13.2 | 54.9 ± 31.6 | 50.0 ± 8.6 | |
| Valine | 417 ± 61 | 422 ± 41 | 412 ± 92 | 414 ± 28 | |
| Leucine | 1798 ± 301 | 1749 ± 154 | 1659 ± 401 | 1761 ± 134 | |
| Isoleucine | 1047 ± 152 | 1049 ± 92 | 1002 ± 247 | 997 ± 123 | |
| Threonine | 166 ± 29 | 167 ± 11 | 141 ± 25 | 211 ± 14 | * |
| Glycine | 582 ± 60 | 217 ± 33 | 486 ± 74 | 171 ± 18 | * |
| Serine | 51 ± 9 | 34 ± 4 | 39 ± 5 | 36 ± 5 | |
| Alanine | 1037 ± 94 | 826 ± 128 | 989 ± 179 | 1230 ± 100 | |
| Glutamic Acid | 104 ± 18 | 123 ± 12 | 92 ± 14 | 187 ± 32 | * |
| Glutamine | 2891 ± 208 | 2470 ± 318 | 1835 ± 258 | 2783 ± 86 | * |
| Proline | 683 ± 116 | 776 ± 104 | 728 ± 174 | 1835 ± 261 | * |
| Aspartic Acid | 24.7 ± 3.3 | 29.0 ± 3.6 | 25.0 ± 3.7 | 36.1 ± 2.6 | |
| Aspargine | 6.0 ± 1.1 | 8.4 ± 3.4 | 3.7 ± 1.2 | 8.8 ± 1.8 | |
| Methionine | 81.0 ± 16.5 | 65.9 ± 8.2 | 53.5 ± 6.2 | 75.2 ± 7.1 | |
| Cysteine | 18.6 ± 6.1 | 27.0 ± 15.1 | 28.1 ± 9.7 | 26.7 ± 10.0 | |
| Phenylalanine | 296 ± 60 | 283 ± 30 | 271 ± 36 | 279 ± 18 | |
| Tyrosine | 14.7 ± 5.8 | 14.3 ± 4.0 | 12.9 ± 3.4 | 17.1 ± 3.2 | |
| Tryptophan | 33.2 ± 15.4 | 33.2 ± 12.6 | 24.4 ± 8.4 | 16.2 ± 6.1 | |
| Histidine | 1.99 ± 0.76 | 2.32 ± 0.96 | 2.95 ± 1.1 | 1.5 ± 0.3 | |
| Ornithine | 11.7 ± 2.7 | 10.0 ± 2.0 | 10.7 ± 2.1 | 11.4 ± 2.0 | |
| Lipid Metabolites | | | | | |
| Phosphate | 14724 ± 801 | 15003 ± 1007 | 13232 ± 640 | 13590 ± 270 | |
| Diphosphate | 1968 ± 402 | 5183 ± 2133 | 1636 ± 161 | 2930 ± 608 | * |
| Phosphoglycerol | 11517 ± 299 | 10969 ± 790 | 9647 ± 334 | 11729 ± 395 | |
| 3-Phosphoglycerate | 471 ± 84 | 438 ± 87 | 205 ± 27 | 204 ± 24 | * |
| 2-Phosphoglycerate | 27.4 ± 4.3 | 23.4 ± 2.9 | 15.0 ± 1.5 | 13.0 ± 1.3 | * |
| DHAP | 7.47 ± 1.05 | 6.78 ± 0.46 | 5.53 ± 0.53 | 5.87 ± 0.60 | |
| Inositol | 2964 ± 266 | 2030 ± 119 | 2283 ± 175 | 1940 ± 165 | |
| Myo-inositol Phosphate | 345 ± 70 | 465 ± 109 | 258 ± 13 | 363 ± 74 | * |

TABLE 1-continued

Metabolomic Analysis of Liver Tissue by GC-MS
GC-MS data presented here are in arbitrary units and expressed as mean ± sem
Metabolites shown in orange background with an asterisk on the right end of the line have
interesting or significant trends with respect to genotype or dietary regimen or both.

|  | WT-CNT | WT-HFD | KO-CNT | KO-HFD |  |
|---|---|---|---|---|---|
| Lauric Acid | 37.5 ± 3.0 | 37.2 ± 3.6 | 32.6 ± 1.5 | 35.4 ± 2.0 |  |
| Myristic Acid | 87.8 ± 10.3 | 73.5 ± 5.5 | 87.1 ± 8.7 | 63.0 ± 5.5 | * |
| Palmitaladic Acid | 73.3 ± 17.0 | 40.4 ± 6.9 | 89.3 ± 23.5 | 24.4 ± 5.7 | * |
| Palmitic Acid | 6714 ± 1091 | 7911 ± 1181 | 6285 ± 967 | 7838 ± 1014 |  |
| Linoelic Acid | 667 ± 143 | 759 ± 159 | 560 ± 145 | 572 ± 106 |  |
| Oleic Acid | 670 ± 138 | 851 ± 141 | 635 ± 171 | 662 ± 117 |  |
| Elaidic Acid | 120 ± 25 | 126 ± 28 | 175 ± 33 | 87 ± 18 | * |
| Stearic Acid | 2662 ± 462 | 4471 ± 682 | 2206 ± 344 | 3892 ± 559 | * |
| Arachidonic Acid | 56.0 ± 10.6 | 62.5 ± 15.4 | 46.4 ± 2.1 | 54.8 ± 6.8 |  |
| 1-Monooleoylglycerol | 368 ± 85 | 498 ± 113 | 377 ± 129 | 475 ± 53 |  |
| 1-monostearylglycerol | 1727 ± 367 | 2879 ± 502 | 1428 ± 337 | 2696 ± 289 | * |
| 1-Monopalmitoylglycerol | 3808 ± 741 | 4606 ± 880 | 3645 ± 736 | 5011 ± 609 |  |
| 1-Monopalmitoylylglycerol | 26.1 ± 6.0 | 23.6 ± 6.7 | 36.3 ± 10.8 | 16.5 ± 2.6 | * |
| Cholesterol | 1316 ± 113 | 1416 ± 163 | 1146 ± 126 | 1367 ± 109 |  |
| Nucleic Acid Metabolites | | | | | |
| Xanthine | 1133 ± 129 | 1183 ± 167 | 972 ± 83 | 940 ± 150 |  |
| Adenosine | 1.87 ± 0.33 | 1.82 ± 0.31 | 2.45 ± 0.26 | 2.16 ± 0.24 |  |
| Inosine | 394 ± 50 | 295 ± 50 | 276 ± 30 | 217 ± 52 | * |
| Adenine | 146 ± 13 | 153 ± 12 | 127 ± 4 | 167 ± 17 | * |
| Uracil | 42.7 ± 11.9 | 54.3 ± 9.0 | 21.6 ± 2.8 | 292.8 ± 98 |  |

Significant differences and interesting trends have been noted in several of these metabolites as shown with respect to genotype (WT vs. KO) or the diet (regular diet vs. high-fat diet) or both variables.

Based on the data disclosed herein, it appears that the KO mice are resistant to high-fat diet-induced obesity. There are three possible explanations for this. The first possibility is a decreased appetite leading to less consumption of food. A second possibility is a lack of absorption of fat in the digestive system. Finally, the third possibility is increased ability to burn more calories due to higher energy metabolism.

In the studied presented, the first two possibilities were eliminated, i.e, the KO mice were not eating less food than the WT mice, and the KO mice had well-formed stools with no evidence of steatorrhea. This leaves the third possibility, i.e., increased ability to burn more calories or higher energy metabolism. To confirm this, the expression of key genes in the WT and KO mice under basal or normal conditions, i.e., without feeding high-fat diet, were examined.

FIG. 14 shows the expression of two groups of key molecules involved in energy metabolism in the brown fat, which is rich in mitochondria. These are the PPARs (peroxisome proliferator-activated receptor), the nuclear receptors, involved in the regulation of inflammation and energy homeostasis and thus represent important targets for obesity and metabolic syndrome.

PPAR-α knockout mice are known to gain more adipose tissue mass as compared to the wild type mice. PPAR-γ plays a role in adipocyte differentiation, and reduces inflammatory gene expression. Less is known about the role of PPAR-δ in obesity, but it stimulates fatty acid oxidation.

As shown in the left panel of FIG. 14, PPAR-γ and PPAR-δ expression levels in KO mice are significantly higher as compared to the WT mice, while the expression of PPAR-α did not differ. Thus, the observed resistance of the KO mice to diet-induced obesity is partly related to the differences in baseline expression of the PPAR isoforms in these mice as compared to the WT mice.

Another potential group of molecules considered were the mitochondrial uncoupling proteins (UCPs). UCPs are themogenic proteins and regulate energy expenditure. They uncouple mitochondrial respiration for oxidative phosphorylation (formation of ATP), resulting in dissipation of energy as heat, instead of converting into storage form of energy. UCPs play a role in the development of obesity and type II diabetes mellitus. As shown in the right panel of FIG. 14, the basal expression levels of all three UCPs in the brown fat of KO mice are significantly higher as compared to the expression levels in WT mice. This advocates for the conclusion that KO mice are inherently capable of burning extra calories consumed in the food.

The enlarged fat cells in the white adipose tissue in obesity recruit macrophages (inflammatory cells) and promote inflammation, leading to elaboration of various cytokines (inflammatory molecules) and chemical mediators. Accordingly, the inflammatory mediators in the white fat of the WT and KO mice were examined after feeding high-fat diet for 16 weeks. As shown in the left panel of FIG. 15, the expression levels of IL-6 (interleukin-6, an inflammatory cytokine), MCP-1 (monocyte chemoattractant protein-1 or CCL2) and its receptor (CRR2), CD68 (monocyte/macrophage cluster differentiation 68 protein), as well as F4/80 (a defining marker of murine macrophages) were significantly lower in the KO mice as compared to the WT mice. This suggests a lesser degree of inflammation in the white adipose tissue of KO mice versus WT mice after feeding high-fat diet.

During the study, the expression of insulin receptor substrate (IRS) 1 and 2 was examined. These receptors transmit signals from the insulin receptor and insulin-like growth factor-1 (IGF-1), and thus play an important role in metabolic pathways. Mice lacking IRS1 develop a mild diabetic phenotype, whereas the mice lacking IRS2 have a diabetic phenotype. As shown in the right panel of FIG. 15, the IRS1 expression was markedly higher in the KO mice fed high-fat diet versus WT mice fed high-fat diet, whereas the expression levels of IRS2 did not differ between these two genotypes. This finding suggests that IRS1 contributes to the observed resistance of the KO mice to diet-induced obesity.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A method for treating diet-induced obesity in a subject by administering an agent that blunts the expression or activity of the P2Y2 receptor in the subject so as to treat diet-induced obesity in the subject.

2. The method of claim 1, wherein the agent inhibits the P2Y2 receptor and is a selective P2Y2 receptor antagonist which is a small non-nucleic acid organic molecule.

3. The method of claim 1, wherein the agent is an oligonucleotide that is capable of hybridizing under physiological conditions to a RNA that encodes a P2Y2 receptor.

4. The method of claim 3, wherein the oligonucleotide is an antisense oligonucleotide.

5. The method of claim 3, wherein the oligonucleotide is a ribozyme.

6. The method of claim 4, wherein the oligonucleotide is an inhibitory RNA.

7. The method of claim 6, wherein the inhibitory RNA is a small inhibitory RNA (siRNA).

* * * * *